United States Patent
Den Boef

(10) Patent No.: US 7,580,131 B2
(45) Date of Patent: Aug. 25, 2009

(54) ANGULARLY RESOLVED SCATTEROMETER AND INSPECTION METHOD

(75) Inventor: Arie Jeffrey Den Boef, Waalre (NL)

(73) Assignee: ASML Netherlands B.V., Veldhoven (NL)

( * ) Notice: Subject to any disclaimer, the term of this patent is extended or adjusted under 35 U.S.C. 154(b) by 122 days.

(21) Appl. No.: 11/785,426

(22) Filed: Apr. 17, 2007

(65) Prior Publication Data

US 2008/0259343 A1    Oct. 23, 2008

(51) Int. Cl.
*G01N 21/47* (2006.01)
*G01B 11/00* (2006.01)

(52) U.S. Cl. ............... 356/446; 356/445; 356/401; 356/237.2

(58) Field of Classification Search ......... 356/445–447, 356/237.2, 426–427, 626, 629, 639–640, 356/401; 250/559.07, 559.22, 559.39, 559.49, 250/548; 73/82, 865.8, 866.5, 865.5; 359/355, 359/364, 365
See application file for complete search history.

(56) References Cited

U.S. PATENT DOCUMENTS

| | | | | |
|---|---|---|---|---|
| 6,130,750 A | * | 10/2000 | Ausschnitt et al. | ........... 356/401 |
| 6,512,631 B2 | * | 1/2003 | Shafer et al. | ................. 359/355 |
| 6,801,358 B2 | * | 10/2004 | Shafer et al. | ................. 359/355 |
| 7,106,454 B2 | * | 9/2006 | De Groot et al. | ............ 356/511 |
| 7,136,159 B2 | * | 11/2006 | Tsai et al. | ................. 356/237.5 |
| 2006/0066855 A1 | * | 3/2006 | Boef et al. | ................... 356/401 |

* cited by examiner

*Primary Examiner*—Sang Nguyen
(74) *Attorney, Agent, or Firm*—Sterne, Kessler, Goldstein & Fox P.L.L.C.

(57) ABSTRACT

In an angularly resolved scatterometer, an aperture plate including at least one obscuration extending into the image of the pupil plane is provided. Defocus values of a target pattern are determined from the radial distance between the innermost point of the images of the obscurations and the nominal center if the pupil image. Defocus errors are compensated for by capturing a plurality of normalization images using a reference plate at a plurality of different defocus positions and subtracting a suitable normalization from the measurement spectrum of a target pattern.

20 Claims, 3 Drawing Sheets

ANGULARLY RESOLVED SCATTEROMETER AND INSPECTION METHOD

FIELD

The present invention relates to methods of inspection usable, for example, in the manufacture of devices by lithographic techniques and to methods of manufacturing devices using lithographic techniques.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g. including part of, one, or several dies) on a substrate (e.g. a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti-parallel to this direction. It is also possible to transfer the pattern from the patterning device to the substrate by imprinting the pattern onto the substrate.

In order to monitor the lithographic process, it is desirable to measure parameters of the patterned substrate, for example the overlay error between successive layers formed in or on it. There are various techniques for making measurements of the microscopic structures formed in lithographic processes, including the use of scanning electron microscopes and various specialized tools. One form of specialized inspection tool is a scatterometer in which a beam of radiation is directed onto a target on the surface of the substrate and properties of the scattered or reflected beam are measured. By comparing the properties of the beam before and after it has been reflected or scattered by the substrate, the properties of the substrate can be determined. This can be done, for example, by comparing the reflected beam with data stored in a library of known measurements associated with known substrate properties. Two main types of scatterometer are known. Spectroscopic scatterometers direct a broadband radiation beam onto the substrate and measure the spectrum (intensity as a function of wavelength) of the radiation scattered into a particular narrow angular range. Angularly resolved scatterometers use a monochromatic radiation beam and measure the intensity of the scattered radiation as a function of angle.

In an angularly resolved scatterometer, the target being measured or a fiducial used for calibration or normalization is in focus. To this end, an optical, e.g. a Foucault knife edge, or capacitive focus sensor may be provided. However, when using such a sensor, small focus errors (defocus) may remain, e.g. due to process effects related to the structure on the substrate being measured or due to settling time. Such small residual defocus should not, in theory, lead to measurement errors in this type of scatterometer. However, the present inventor has determined that residual defocus does cause measurement errors.

SUMMARY

It is desirable to provide an angularly resolved scatterometer and scatterometry method that do not exhibit, or exhibit to a lesser extent, measurement errors due to residual defocus.

According to an embodiment of the invention, there is provided an inspection method to determine a value related to a parameter of a target pattern printed on a substrate by a lithographic process used to manufacture a device layer on a substrate, the method including: using an optical system including a high-NA objective lens having an object plane and a pupil plane to direct a first beam of radiation on to the target pattern, to collect radiation reflected or scattered by the target pattern and to project a second beam of radiation to form an image of the pupil plane of the objective lens in an image plane; providing an aperture member in the path of the second beam at a location not congruent with the pupil plane of the objective lens, the aperture member defining at least one obscuration extending a predetermined distance into the second beam so as to form a dark area in the image of the pupil plane; determining a radial distance between a radially innermost point of the or each dark area and a nominal center of the image of the pupil plane; and determining an axial distance between the target and the object plane from the determined radial distance(s).

According to an embodiment of the invention, there is provided an inspection method to determine a value related to a parameter of a target pattern printed on a substrate by a lithographic process used to manufacture a device layer on a substrate, the method including: using an optical system including a high-NA objective lens having an object plane and a pupil plane to direct a first beam of radiation on to a reference member, to collect radiation reflected or scattered by the reference member and to project a second beam of radiation to form an image of the pupil plane of the objective lens in an image plane; relatively moving the reference member and the optical system in the direction substantially perpendicular to the object plane so as to position the reference member at a plurality of positions having different distances from the object plane; when the reference member is positioned at each of the plurality of positions, capturing a scatterometric spectra of the reference member; storing the scatterometric spectra of the reference member as a plurality of normalization spectra; using the optical system to direct the first beam of radiation on to the target pattern, to collect radiation reflected or scattered by the target pattern and to project a second beam of radiation to form an image of the pupil plane of the objective lens in an image plane; capturing a scatterometric spectra of the target pattern; determining the distance between the target pattern and the object plane; obtaining a normalization spectrum based on the determined distance between the target pattern and the object plane; normalizing the spectrum of the target pattern using the obtained normalization spectrum to obtain a normalized spectrum; and determining the value related to the parameter from the normalized spectrum.

According to an embodiment of the invention, there is provided an inspection method using a scatterometer to determine a value related to a parameter of a target pattern printed on a substrate by a lithographic process used to manufacture a device layer on a substrate, the method including: obtaining a plurality of normalization spectra using a reference member in the scatterometer in place of the substrate, the normalization spectra being obtained with the reference member positioned at various different defocus values; obtaining a measurement spectrum for the target pattern using the scatterometer; determining the defocus value at the time the measurement spectrum was obtained; normalizing the measurement spectrum using a normalization spectrum corresponding to the determined defocus value to obtain a normalized spectrum; determining the value related to a parameter from the normalized spectrum.

According to an embodiment of the invention, there is provided an inspection method using a scatterometer to determine a value related to a parameter of a target pattern printed on a substrate by a lithographic process used to manufacture a device layer on a substrate, the scatterometer including an optical system including a high-NA objective lens having an object plane and a pupil plane to direct a first beam of radiation on to the target pattern, to collect radiation reflected or scattered by the target pattern and to project a second beam of radiation to form an image of the pupil plane of the objective lens in an image plane, the method including: obtaining a plurality of normalization spectra using a reference member in the scatterometer in place of the substrate, the normalization spectra being obtained with the reference member positioned at various different defocus values; providing an aperture member in the path of the second beam at a location not congruent with the pupil plane of the objective lens, the aperture member defining at least one obscuration extending a predetermined distance into the second beam so as to form a dark area in the image of the pupil plane; obtaining a measurement spectrum for the target pattern using the scatterometer; determining a radial distance between a radially innermost point of the or each dark area and a nominal center of the image of the pupil plane; determining a defocus value, being an axial distance between the target and the object plane from the determined radial distance(s); normalizing the measurement spectrum using a normalization spectrum corresponding to the determined defocus value to obtain a normalized spectrum; and determining the value related to a parameter from the normalized spectrum.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION

Figure 1:
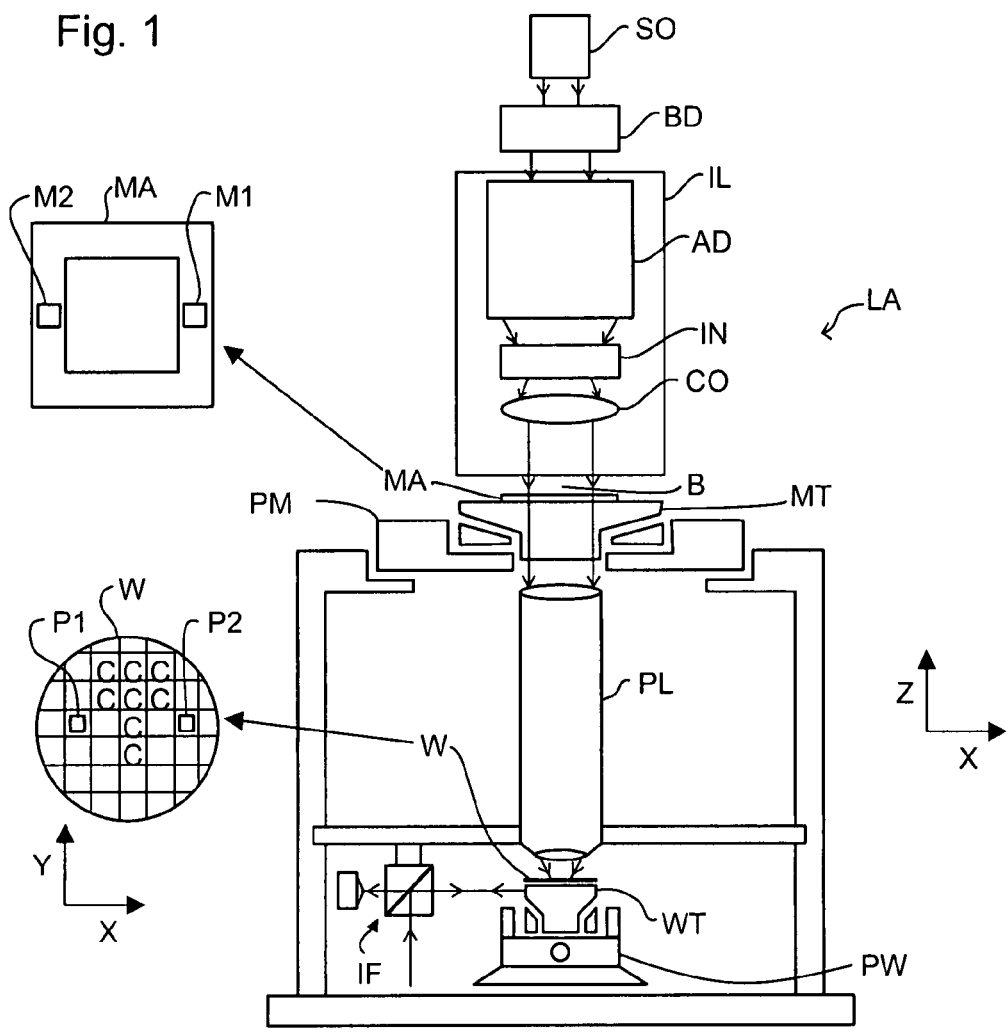
FIG. 1 depicts a lithographic apparatus in accordance with an embodiment of the invention.

FIG. 1 schematically depicts a lithographic apparatus. The apparatus includes: an illumination system (illuminator) IL configured to condition a radiation beam B (e.g. UV radiation or DUV radiation); a support structure or pattern support (e.g. a mask table) MT constructed to support a patterning device (e.g. a mask) MA and connected to a first positioner PM configured to accurately position the patterning device in accordance with certain parameters; a substrate table (e.g. a wafer table) WT constructed to hold a substrate (e.g. a resist-coated wafer) W and connected to a second positioner PW configured to accurately position the substrate in accordance with certain parameters; and a projection system (e.g. a refractive projection lens system) PL configured to project a pattern imparted to the radiation beam B by patterning device MA onto a target portion C (e.g. including one or more dies) of the substrate W.

The illumination system may include various types of optical components, such as refractive, reflective, magnetic, electromagnetic, electrostatic or other types of optical components, or any combination thereof, for directing, shaping, or controlling radiation.

The support structure supports, i.e. bears the weight of, the patterning device. It holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g. employing a transmissive mask). Alternatively, the apparatus may be of a reflective type (e.g. employing a programmable mirror array of a type as referred to above, or employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g. water, so as to fill a space between the projection system and the substrate. An immersion liquid may also be applied to other spaces in the lithographic apparatus, for example, between the patterning device (e.g. mask) and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD including, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may include an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may include various other components, such as an integrator IN and a condenser CO. The illuminator may be used to condition the radiation beam, to have a desired uniformity and intensity distribution in its cross-section.

The radiation beam B is incident on the patterning device (e.g., mask MA), which is held on the support structure (e.g., mask table) MT, and is patterned by the patterning device. Having traversed the patterning device (e.g. mask) MA, the radiation beam B passes through the projection system PL, which focuses the beam onto a target portion C of the substrate W. With the aid of the second positioner PW and position sensor IF (e.g. an interferometric device, linear encoder, 2-D encoder or capacitive sensor), the substrate table WT can be moved accurately, e.g. so as to position different target portions C in the path of the radiation beam B. Similarly, the first positioner PM and another position sensor (which is not explicitly depicted in FIG. 1a) can be used to accurately position the patterning device (e.g. mask) MA with respect to the path of the radiation beam B, e.g. after mechanical retrieval from a mask library, or during a scan. In general, movement of the mask table MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the support structure (e.g. mask table) MT may be connected to a short-stroke actuator only, or may be fixed. Patterning device (e.g. mask) MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the patterning device (e.g. mask) MA, the mask alignment marks may be located between the dies.

The depicted apparatus could be used in at least one of the following modes:

1. In step mode, the support structure or pattern support (e.g. mask table) MT and the substrate table WT are kept essentially stationary, while an entire pattern imparted to the radiation beam is projected onto a target portion C at one time (i.e. a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the support structure or pattern support (e.g. mask table) MT and the substrate table WT are scanned synchronously while a pattern imparted to the radiation beam is projected onto a target portion C (i.e. a single dynamic exposure). The velocity and direction of the substrate table WT relative to the support structure (e.g. mask table) MT may be determined by the (de-)magnification and image reversal characteristics of the projection system PL. In scan mode, the maximum size of the exposure field limits the width (in the non-scanning direction) of the target portion in a single dynamic exposure, whereas the length of the scanning motion determines the height (in the scanning direction) of the target portion.

3. In another mode, the support structure (e.g. mask table) MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 2:
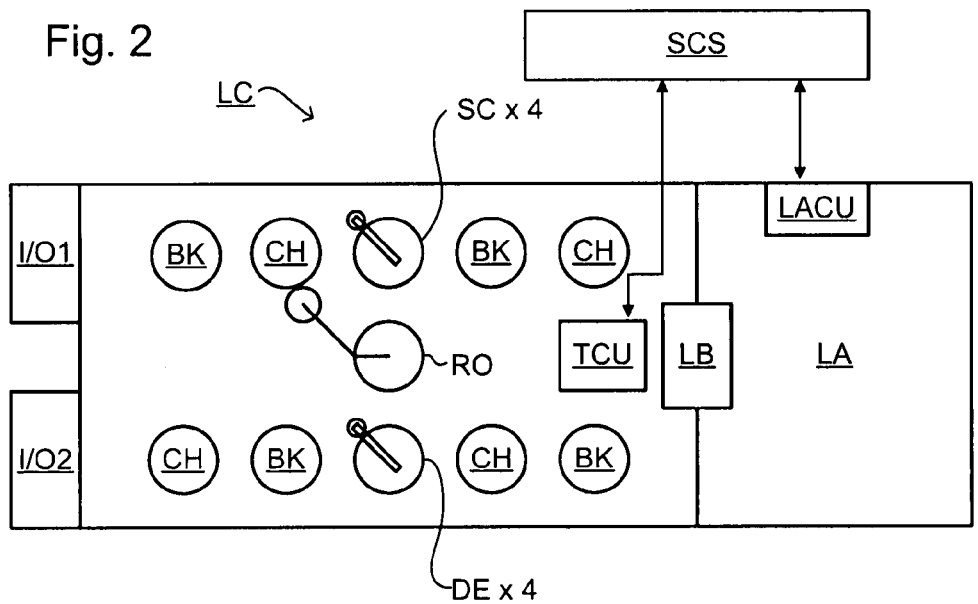
FIG. 2 depicts a lithographic cell or cluster in accordance with an embodiment of the invention.

As shown in FIG. 2, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. If errors are detected, adjustments may be made to exposures of subsequent substrates, especially if the inspection can be done soon and fast enough that other substrates of the same batch are still to be exposed. Also, already exposed substrates may be stripped and reworked—to improve yield—or discarded—thereby avoiding performing exposures on substrates that are known to be faulty. In a case where only some target portions of a substrate are faulty, further exposures can be performed only on those target portions which are good.

An inspection apparatus is used to determine the properties of the substrates, and in particular, how the properties of different substrates or different layers of the same substrate vary from layer to layer. The inspection apparatus may be integrated into the lithographic apparatus LA or the lithocell LC or may be a stand-alone device. To enable most rapid measurements, it is desirable that the inspection apparatus measure properties in the exposed resist layer immediately after the exposure. However, the latent image in the resist has a very low contrast—there is only a very small difference in refractive index between the parts of the resist which have been exposed to radiation and those which have not—and not all inspection apparatus have sufficient sensitivity to make useful measurements of the latent image. Therefore measurements may be taken after the post-exposure bake step (PEB) which is customarily the first step carried out on exposed substrates and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibilities for rework of faulty substrates but may still provide useful information.

Figure 3:
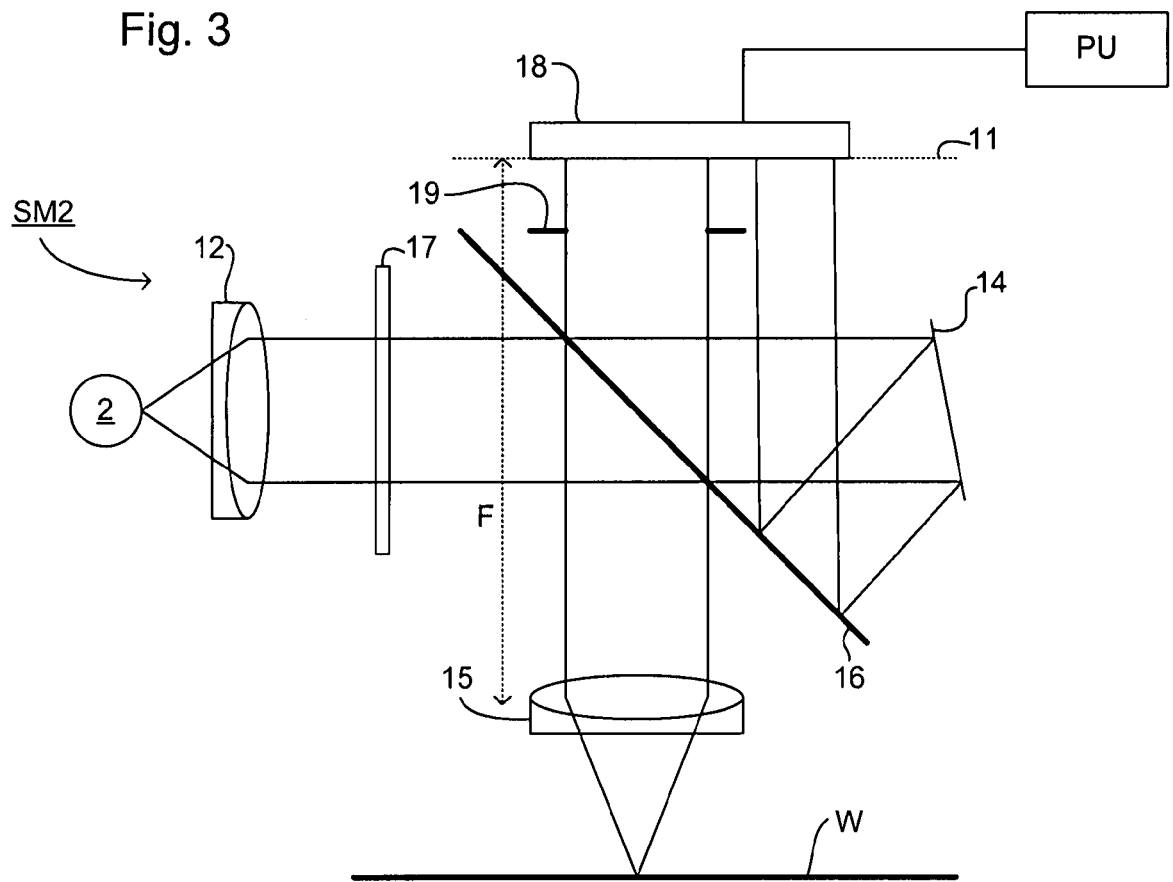
FIG. 3 depicts a scatterometer according to an embodiment of the invention.

A scatterometer SM2 according to an embodiment of the present invention is shown in FIG. 3. In this device, the radiation emitted by radiation source unit 2 is collimated using lens system 12 through polarizer 17, reflected by partially reflected surface 16 and is focused onto substrate W via a microscope objective lens 15, which has a high numerical aperture (NA), preferably at least 0.9 and more preferably at least 0.95. Immersion scatterometers may even have lenses with numerical apertures over 1. The reflected radiation then transmits through partially reflective surface 16 into a detector 18 in order to have the scatter spectrum detected. The detector may be located in the back-projected pupil plane 11, which is at the focal length of the lens system 15, however the pupil plane may instead be re-imaged with auxiliary optics (not shown) onto the detector. The pupil plane is a plane in which the radial position of radiation defines the angle of incidence and the angular position defines azimuth angle of the radiation. The detector is preferably a two-dimensional detector so that a two-dimensional angular scatter spectrum of the substrate target can be measured. The detector 18 may be, for example, an array of CCD or CMOS sensors, and may use an integration time of, for example, 40 milliseconds per frame.

A reference beam is often used for example to measure the intensity of the incident radiation. To do this, when the radiation beam is incident on the beam splitter 16 part of it is transmitted through the beam splitter as a reference beam towards a reference mirror 14. The reference beam is then projected onto a different part of the same detector 18.

The detector 18 may measure the intensity of scattered light at a single wavelength (or narrow wavelength range), the intensity separately at multiple wavelengths or integrated over a wavelength range. Furthermore, the detector may separately measure the intensity of transverse magnetic- and transverse electric-polarized light and/or the phase difference between the transverse magnetic- and transverse electric-polarized light.

The target on substrate W may be a grating, which is printed such that after development, the bars are formed of solid resist lines. The bars may alternatively be etched into the substrate. This pattern is sensitive to aberrations in the lithographic projection apparatus, particularly the projection system PL, and illumination symmetry and the presence of such aberrations will manifest themselves in a variation in the printed grating. Accordingly, the scatterometry data of the printed gratings is used to reconstruct the gratings. The parameters of the grating, such as line widths and shapes, may be input to the reconstruction process, performed by processing unit PU, from knowledge of the printing step and/or other scatterometry processes. Other forms of target may be used to measure other parameters of structures on the substrate or the processes used to produce them.

The present inventor has determined that in an angularly resolved scatterometer, measurement errors due to residual defocus can be caused by dirt and/or imperfections in the optical elements in the measurement branch (that is the optical path from target to detector) of the scatterometer. In particular, the errors in the recorded spectra due to dirt and imperfections increase towards the outer edge of the pupil plane, which is where much of the information used for measurements is often to be found. To address this problem the present embodiment employs a novel focus error detection arrangement and employs a novel error compensation method which are described below in turn. Although the focus error detection arrangement and the focus error compensation method may be used independently to advantage, a particularly beneficial effect is obtained when they are used together.

Figure 4:
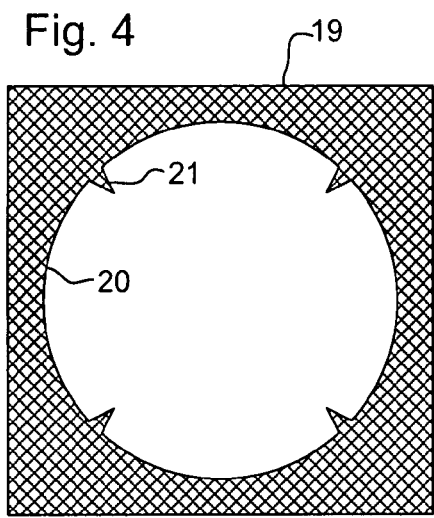
FIG. 4 depicts an aperture plate.

For focus error detection in the embodiment of the invention, a particular aperture member 19 is placed in the measurement branch at a location optically away from the pupil plane, e.g. after optics that re-image the pupil plane on the sensor. The aperture member 12 is positioned in a path of the beam of radiation at a location not congruent with the pupil plane of the lens system. The aperture member is shown in FIG. 4 and has a central transparent region 20 with a diameter larger than the nominal pupil diameter. One or more obscurations 21 project inwardly so that they are visible in the pupil image recorded by the detector 18. In a preferred embodiment the obscurations are substantially opaque, but they may be partially transmissive as long as they are sufficiently opaque to form discernible shadows on the detector. In the figure, four triangular obscurations are shown at azimuth angles of about +/−45° and about +/−135° but the obscurations do not need to be triangular and do not need to be at these positions. Other than that they are visible in the pupil image and the position of the image detectably changes with defocus, the only requirements on the shape and position of the obscurations is that they do not obscure too much useful information in the pupil image. A particularly preferred form of obscuration is a set of lines or arcs parallel to the edge of the pupil or the tangent to edge of the pupil so that a grating is formed on the detector. Radial shifts in this grating can be measured very accurately by comparing the image of the shadow with a reference image to form a phase grating. Multiple, azimuthally spaced obscurations allow elimination of tilt effects from the measurement of defocus by differential measurements. Additional obscurations are useful to allow averaging to reduce errors. The aperture member may be provided with an actuator (not shown) to enable it to be selectively removed from the beam path.

Figure 5:
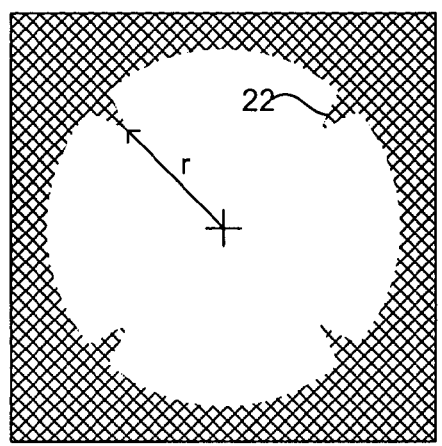
FIG. 5 depicts an image of the aperture plate of FIG. 4 in the detector of the scatterometer of FIG. 3.

FIG. 5 shows the image of the aperture 19 on the detector 18. The image of the obscurations 21 is blurred and the radial position r of their ends (radially innermost points), or another discernable point on each image, depends on the amount of defocus of the substrate or fiducial being measured. The distance r can be determined by an image recognition algorithm executed by the processing unit PU. By appropriate calibration, for example, a relationship between r and defocus can be obtained. Having determined the defocus value, appropriate corrections can be made, e.g. by adjusting the position of the substrate or fiducial being measured. The above described method of determining defocus has the benefits that it is accurate and can be performed quickly so that there is no loss of throughput. Furthermore, the measurement of defocus can be obtained off-line from images of the pupil plane captured to make measurements on the target so that the defocus values are exactly contemporaneous with the parameter measurements, avoiding all data aging issues.

Figure 6:
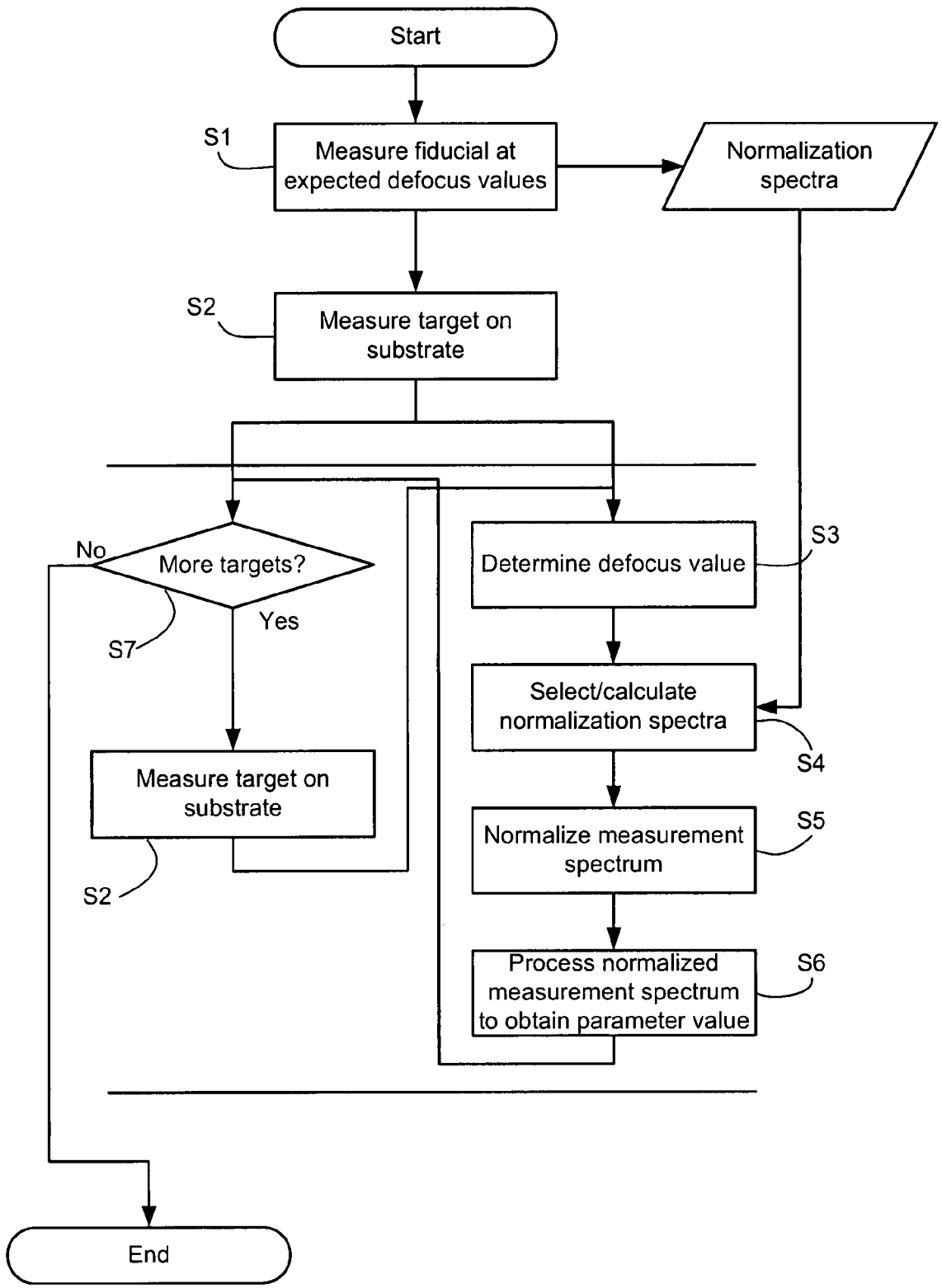
FIG. 6 is a flow chart depicting procedures in a method according to an embodiment of the invention.

A novel method of compensating for defocus errors will now be described with reference to FIG. 6. The first procedure, S1, is to capture a set of images of a blank fiducial (e.g. an aluminum plate with low surface roughness) at a variety of different defocus values, both positive and negative, that are expected to occur in use. This can be done by moving the fiducial up and down as necessary. The necessary number of images can be captured, for example, during a substrate exchange or between lots without loss of throughput. Depending on the stability of the optical system, it may not be necessary to capture a set of images that frequently. If multiple wavelengths and/or polarization states are to be used for capturing measurement spectra, for maximum accuracy a set of normalization spectra is obtained for each wavelength and/or polarization state. The captured images and related defocus values are stored in a database as a set of normalization spectra for later use. Images for defocus values between those at which images were captured can be interpolated either in advance or at the time of use. The normalization spectra measure the effect of dirt and/or imperfections in the measurement branch of the optical system.

The target, a parameter of which is to be determined, is measured in procedure S2 to obtain a measurement image or spectra, in the conventional manner. Before processing the measurement spectra to obtain the parameter of interest, the defocus values at the time of the measurements are determined S3, e.g. by the method using aperture 19 described above. Next, in procedure S4, a suitable normalization spectrum is obtained from the database, or interpolated from stored spectra. In procedure S5, the measurement spectra are divided by the selected or calculated normalization spectrum to obtain a normalized spectrum. In procedure S6, the normalized spectra is processed to determine the parameter of interest. This can be done in any suitable manner, known to the person skilled in the art, such as by rigorous coupled wave analysis (RCWA), library search of pre-measured or simulated spectra, iterative methods or principal component analysis (PCA). It is then determined S7 whether there are more targets to measure in which case procedures S2 to S6 are repeated as often as necessary. In general procedure S1, measurement of the fiducial at multiple defocus values, is only repeated no more than once per substrate or batch and in many cases once per day or less frequently will suffice. However, if for any reason, the defocus errors change over a very short timescale, procedure S1 might be repeated each measurement target.

A particular benefit when the above method of compensating for defocus is combined with the above described method of determining defocus is that procedure S3 can be performed from the image captured for measurement purposes and so procedures S3 to S6 can all be carried out off-line and/or in parallel with the acquisition of spectra from other targets so there is no loss of throughput. The fact that the residual defocus can be compensated for by the above described method means that no additional procedures, such as adjusting the position of the substrate relative to the objective lens, need to be taken at the time of image capture.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g. having a wavelength of or about 365, 355, 248, 193, 157 or 126 nm) and extreme ultra-violet (EUV) radiation (e.g. having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

While specific embodiments of the invention have been described above, it will be appreciated that the invention may be practiced otherwise than as described. For example, the invention may take the form of a computer program containing one or more sequences of machine-readable instructions describing a method as disclosed above, or a data storage medium (e.g. semiconductor memory, magnetic or optical disk) having such a computer program stored therein.

The descriptions above are intended to be illustrative, not limiting. Thus, it will be apparent to one skilled in the art that modifications may be made to the invention as described without departing from the scope of the claims set out below.

The invention claimed is:

1. An angularly resolved scatterometer comprising:
   an optical system comprising an objective lens including an object plane and a pupil plane, the optical system arranged to direct a first beam of radiation onto a target pattern of a substrate printed by a lithographic process, to collect radiation reflected or scattered by the target pattern, and to project a second beam of radiation to form an image of the pupil plane of the objective lens in an image plane;

a detector located in the image plane and configured to convert radiation incident on a first portion of the detector into scatterometric spectra;

an aperture member positioned in a path of the second beam of radiation at a location not congruent with the pupil plane of the objective lens, the aperture member defining at least one obscuration extending a predetermined distance into the second beam of radiation so as to form a dark area in the image of the pupil plane; and a reflecting device located in a path of a third beam of radiation and arranged to produce a fourth beam of radiation received at a second portion of the detector, the optical device being configured to direct the third beam of radiation to reflect from the reflecting device to produce the fourth beam of radiation.

2. The angularly resolved scatterometer according to claim 1, wherein the aperture member defines a plurality of obscurations.

3. The angularly resolved scatterometer according to claim 2, wherein the aperture member defines four obscurations.

4. The angularly resolved scatterometer according to claim 2, wherein each of the obscurations extends the same distance into the second beam of radiation.

5. The angularly resolved scatterometer according to claim 2, wherein the plurality of obscurations are evenly spaced azimuthally.

6. The angularly resolved scatterometer according to claim 1, further comprising a processing unit configured to calculate a distance between a radially innermost point of the dark area and a nominal center of the image of the pupil plane.

7. The angularly resolved scatterometer according to claim 6, wherein the processing unit is configured to calculate a distance between the target pattern and the object plane from the calculated distance.

8. The angularly resolved scatterometer according to claim 1, wherein the at least one obscuration comprises a set of parallel arcs or lines parallel to an edge of the pupil plane or a tangent to the edge of the pupil plane at the nearest point thereon.

9. The angularly resolved scatterometer according to claim 1, wherein the objective lens comprises a high-NA objective lens.

10. The angularly resolved scatterometer according to claim 9, wherein the objective lens comprises a high-NA objective lens that has a NA of at least 0.9.

11. The angularly resolved scatterometer according to claim 1, wherein the detector is configured to measure a focus error based on the scatterometric spectra.

12. The angularly resolved scatterometer according to claim 1, wherein the detector is configured to measure an intensity of the third beam of radiation.

13. A method for detecting a focus error in an angularly resolved scatterometer, the method comprising:

directing a first beam of radiation onto a target pattern of a substrate printed by a lithographic process with an optical system, the optical system comprising an objective lens including an objective plane and pupil plane;

collecting radiation reflected or scattered by the target pattern;

projecting a second beam of radiation onto a first portion of a detector, with the optical system, to form an image of the pupil plane of the objective lens in an image plane;

defining at least one obscuration that extends a predetermined distance into the second beam of radiation so as to form a dark area in the image of the pupil plane, the at least one obscuration defined using an aperture member;

converting the second beam of radiation into scatterometric spectra; and directing a third beam of radiation to reflect from a reflecting device in the optical system to produce a fourth beam of radiation to be received at a second portion of the detector.

14. The method according to claim 13, wherein defining the at least one obscuration comprises defining a plurality of obscurations that extend the same distance into the second beam of radiation.

15. The method according to claim 13, wherein defining at least one obscuration comprises defining a plurality of obscurations that are evenly spaced azimuthally.

16. The method of claim 13, further comprising:

determining the distance between a radially innermost point of the dark area and a nominal center of the image of the pupil plane.

17. The method of claim 16, wherein determining comprises determining a distance between the target pattern and the object plane from the determined distance.

18. The method of claim 13, wherein defining the at least one obscuration comprises using a set of parallel arcs or lines parallel to an edge of the pupil plane or a tangent to the edge of the pupil plane at the nearest point thereon to define the at least one obscuration.

19. The method of claim 13, wherein converting the second beam of radiation comprises measuring a focus error in the angularly resolved scatterometer.

20. The method of claim 13, wherein projecting a third beam of radiation comprises measuring an intensity of the third beam of radiation.

* * * * *